United States Patent
Sugiura

(10) Patent No.: US 8,188,743 B2
(45) Date of Patent: May 29, 2012

(54) MAGNETIC RESONANCE IMAGING APPARATUS AND CONTROL METHOD OF MAGNETIC RESONANCE IMAGING APPARATUS

(75) Inventor: Satoshi Sugiura, Otawara (JP)

(73) Assignees: Kabushiki Kaisha Toshiba, Minato-Ku, Tokyo (JP); Toshiba Medical Systems Corporation, Otawara-Shi, Tochigi (JP)

( * ) Notice: Subject to any disclaimer, the term of this patent is extended or adjusted under 35 U.S.C. 154(b) by 314 days.

(21) Appl. No.: 12/555,946

(22) Filed: Sep. 9, 2009

(65) Prior Publication Data

US 2010/0060284 A1   Mar. 11, 2010

(30) Foreign Application Priority Data

Sep. 9, 2008  (JP) ................... 2008-230994
Jul. 23, 2009  (JP) ................... 2009-172049

(51) Int. Cl.
*G01V 3/00* (2006.01)
(52) U.S. Cl. ...................... 324/318; 324/309
(58) Field of Classification Search .......... 324/300–322; 600/407–445
See application file for complete search history.

(56) References Cited

U.S. PATENT DOCUMENTS

| | | | |
|---|---|---|---|
| 6,512,374 B1 * | 1/2003 | Misic et al. | 324/319 |
| 6,724,923 B2 * | 4/2004 | Ma et al. | 382/131 |
| 6,801,036 B2 * | 10/2004 | Meyer | 324/309 |
| 6,972,565 B2 * | 12/2005 | Yokoi et al. | 324/307 |
| 7,190,164 B2 * | 3/2007 | Kuhara | 324/309 |
| 7,368,914 B2 * | 5/2008 | Ikeda et al. | 324/318 |
| 7,375,525 B2 * | 5/2008 | Laubacher et al. | 324/318 |
| 7,423,428 B2 * | 9/2008 | Kuhara | 324/307 |
| 7,626,385 B2 * | 12/2009 | Yokoi et al. | 324/307 |
| 7,676,256 B2 * | 3/2010 | Satragno et al. | 600/417 |
| 7,844,318 B2 * | 11/2010 | Rezzonico et al. | 600/410 |
| 2003/0132750 A1 | 7/2003 | Machida et al. | |
| 2008/0204023 A1 | 8/2008 | Du et al. | |
| 2011/0071382 A1 * | 3/2011 | Miyazaki et al. | 600/413 |
| 2011/0291655 A1 * | 12/2011 | Hamamura et al. | 324/318 |

FOREIGN PATENT DOCUMENTS

| | | |
|---|---|---|
| CN | 1450358 A | 10/2003 |
| CN | 101254099 A | 9/2008 |
| JP | 5-065179 | 9/1993 |
| JP | 07-124135 | 5/1995 |
| JP | 2005-124855 | 5/2005 |
| JP | 2007-282735 | 11/2007 |

OTHER PUBLICATIONS

Chinese office action dated Jan. 19, 2011, re Chinese Application No. 200910170732.4.

* cited by examiner

*Primary Examiner* — Brij Shrivastav

(74) *Attorney, Agent, or Firm* — Nixon & Vanderhye PC

(57) ABSTRACT

According to a Magnetic Resonance Imaging (MRI) apparatus, each of buttons provided in a plurality of sections included in a receiving coil receives from an operator a selecting operation of selecting a section in which the button itself is provided. A control unit of a computer system moves a table on which a subject is placed such that the center of the section selected by receiving the selecting operation via the button is positioned at the center of a magnetic field.

26 Claims, 13 Drawing Sheets

MAGNETIC RESONANCE IMAGING APPARATUS AND CONTROL METHOD OF MAGNETIC RESONANCE IMAGING APPARATUS

CROSS-REFERENCE TO RELATED APPLICATIONS

This application is based upon and claims the benefit of priority from the prior Japanese Patent Application No. 2008-230994, filed on Sep. 9, 2008, and No. 2009-172049, filed on Jul. 23, 2009; the entire contents of which are incorporated herein by reference.

BACKGROUND OF THE INVENTION

1. Field of the Invention

The present invention relates to a magnetic resonance imaging apparatus that images the inside of a subject by using a magnetic resonance phenomenon, and a control method of the magnetic resonance imaging apparatus. The present invention particularly relates to a technology for easily setting a table on which a subject is placed to a target position.

2. Description of the Related Art

A magnetic resonance imaging method is a method of acquiring chemical and physical microscopic information about a substance by using a magnetic resonance phenomenon. The magnetic resonance phenomenon is a phenomenon that when being placed in a magnetic field, an aggregation of subject nuclear spins resonates with a radio-frequency magnetic field in which each atomic nucleus spins at a particular frequency (resonance frequency) responding to its own unique magnetic moment and an existing magnetic field, and generates a signal (magnetic resonance signal) in a relaxation process.

A magnetic resonance imaging apparatus using such magnetic resonance imaging method needs to position a receiving coil for receiving a magnetic resonance signal and the center of a magnetic field that is to be a reference when applying a gradient magnetic field. In other words, matching the center of the receiving coil to the center of the magnetic field is a requirement to obtain a highly accurate Magnetic Resonance (MR) image.

The reason for this is because a static magnetic field generated by a magnet and a gradient magnetic field generated by a gradient magnetic-field coil are both very difficult to be made spatially wholly uniform; uniformity of the static magnetic field and linearity of the gradient magnetic field are made generally ideal at the center, and getting more degraded with the periphery approaching, so that an image taken in the vicinity of the periphery has unsatisfactory fat suppression due to ununiformity of the static magnetic field and image distortion caused by non-linearity of the gradient magnetic field. Such degradation in the image quality often influences a diagnosis if exceeding a certain level.

Conventional positioning of a receiving coil and a table on which a subject is placed, for example, in a case of a coil used as a receiving coil for an abdomen, is performed by a method that, to begin with, the center of the receiving coil is placed on a subject's portion to be scanned, and furthermore, the scan portion is positionally adjusted with a projection light emitted by a projector for positioning, and then the table is moved to the center of a magnetic field. The method needs doubled operations and confirmations, so that it requires time and efforts.

Particularly, a table moving operation of matching a light emitted by the projector with a target position is difficult to perform through only one time of execution of start and stop of a move. Therefore, usually, it is required complicated operations of performing rough setting first, and then switching the movement speed of the table to a low speed, and repeating a fine adjustment of the table forward and backward. If using a projector that uses a laser light, when eyeballs of a subject pass under the projector, an attention needs to be made, for example, blocking out the projector or instructing the subject to close his/her eyes, in order to protect eyeballs.

If performing a scan by using a coil including a plurality of elements, such as a phased array coil; in order to perform the scan at the most sensitive position for the receiving coil element, and to prevent interference of any signal from an unwanted site, the positions of the coil elements to be used need to be accurately matched with the center of the magnetic field.

To solve such problems, for example, JP-A H7-124135 (KOKAI) discloses a method according to which a marker that generates an MR signal is provided at the center of a receiving coil; the position of the marker is obtained by collecting an MR signal from the marker, and then positioning of the receiving coil is performed. FIG. 15 is a schematic diagram for explaining a conventional method of positioning a receiving coil by using a marker. As shown in the figure, according to the method, an MR signal is collected by applying a readout gradient magnetic field $G_R$ [Hz/cm] of which a magnetic field in the z-axis direction is zero at the center of the magnetic field. As a result, when the frequency of the MR signal collected from the marker is $f_0+\Delta f$ [Hz] ($f_0$ is the center frequency), a distance d between the center of the magnetic field and the marker is obtained by $d=(f_0+\Delta f-f_0)/G_R$ [cm].

Moreover, JP-A 2005-124855 (KOKAI) discloses a method of inserting a table on which a subject is placed to a desired position by using a combination of a light emitting element mounted on the upper surface of a receiving coil and a light receiving element mounted at the opening of a gantry. Furthermore, JP H5-65179 (KOKAI) discloses a unit that sets a region of interest on an image displayed on a monitor, and selects one of Radio Frequency (RF) coils. Moreover, JP-A 2007-282735 (KOKAI) discloses a method according to which a light emitting unit for guiding a subject is provided on a receiving coil in use, so that a subject can appropriately follow an instruction from an operator.

However, JP-A H7-124135 (KOKAI) does not propose any unit for an operator to select easily an element to be set at the center of the magnetic field when the receiving coil includes a plurality of elements. Moreover, according to the method disclosed in JP-A 2005-124855 (KOKAI), when a receiving coil includes a plurality of elements, or a plurality of receiving coils are simultaneously installed, a slide amount of the table cannot be set in accordance with the position of an element to be used from among them.

Furthermore, according to the method disclosed in JP H5-65179 (KOKAI), a scan position cannot be specified before collecting any image, so that it is impossible to specify the position of the table prior to a scan, so that an object to eliminate time and effort required in a procedure using a projector when inserting the table cannot be achieved. Moreover, JP-A 2007-282735 (KOKAI) does not propose any unit for the operator to select a receiving element of the RF coil prior to the insertion of the table.

BRIEF SUMMARY

According to one aspect of the present exemplary embodiment, a magnetic resonance imaging apparatus includes a plurality of coils that receives a magnetic resonance signal irradiated from a subject; a receiving coil that includes the plurality of coils; a coil selecting unit that is provided in the receiving coil, and receives from an operator a selecting operation of selecting a coil from among the plurality of coils; and a control unit that moves a table on which the subject is placed such that the coil selected by receiving the selecting operation by the coil selecting unit is positioned at a center of a magnetic field.

According to another aspect of the present exemplary embodiment, a method of controlling a magnetic resonance imaging apparatus, the method includes receiving from an operator a selecting operation of selecting at least one coil from among a plurality of coils included in a receiving coil that receives a magnetic resonance signal irradiated from a subject, and moving a table on which the subject is placed such that the coil selected by receiving the selecting operation is positioned at a center of a magnetic field.

DETAILED DESCRIPTION OF THE INVENTION

Exemplary embodiments of a magnetic resonance imaging apparatus and a control method of the magnetic resonance imaging apparatus according to the present invention will be explained below, in detail with reference to the accompanying drawings. A Magnetic Resonance Imaging apparatus is referred to as an MRI apparatus, and a Magnetic Resonance signal is referred to as an MR signal in the embodiments explained below.

Figure 1:
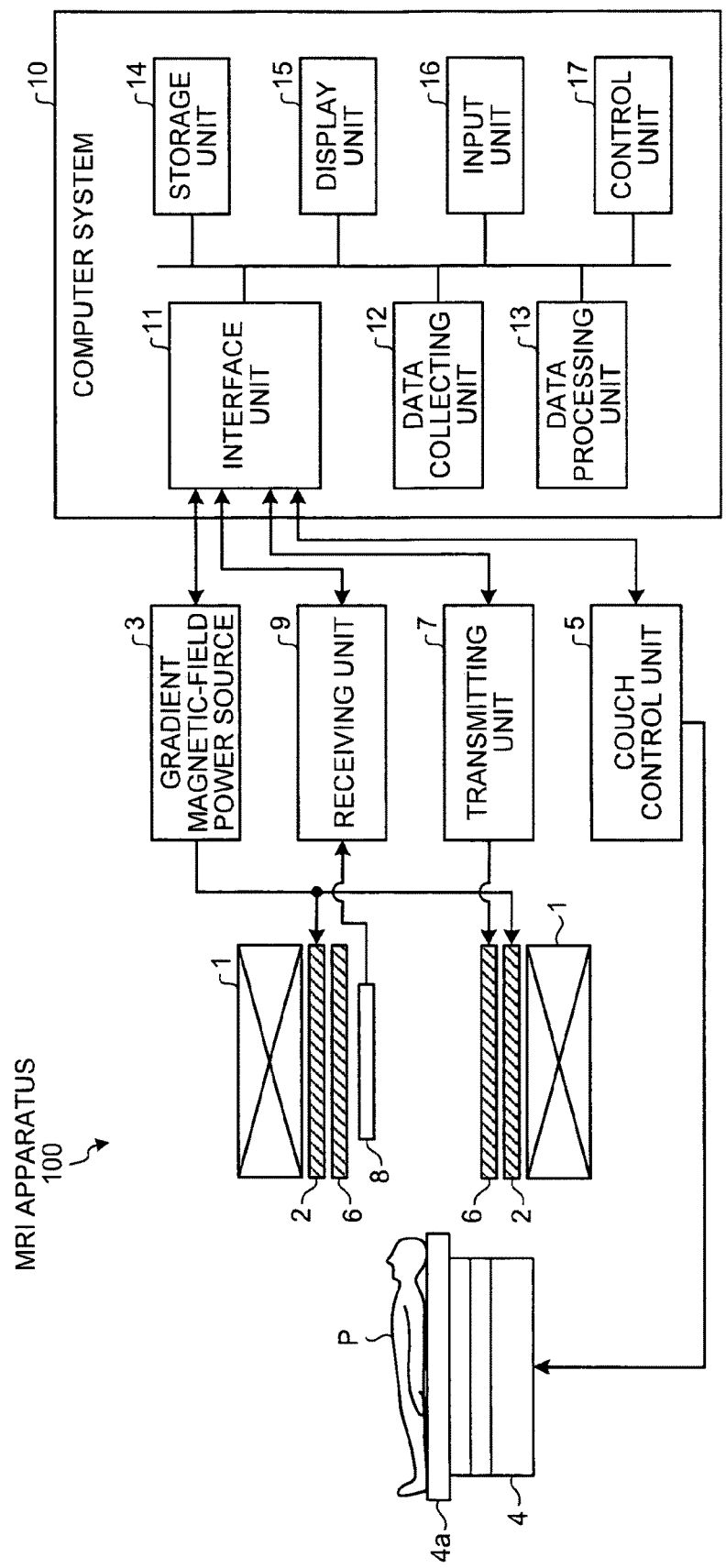
FIG. 1 is a schematic diagram of a Magnetic Resonance Imaging (MRI) apparatus according to a first embodiment of the present invention.

First of all, a configuration of the MRI apparatus according to the first embodiment is explained below with reference to FIG. 1. FIG. 1 is a schematic diagram of a configuration of the MRI apparatus according to the first embodiment. As shown in the figure, an MRI apparatus 100 according to the first embodiment includes a static magnetic-field magnet 1, a gradient magnetic-field coil 2, a gradient magnetic-field power source 3, a couch 4, a couch control unit 5, a transmitting coil 6, a transmitting unit 7, a receiving coil 8, a receiving unit 9, and a computer system 10.

The static magnetic-field magnet 1 is formed in a hollow cylindrical shape, and generates a uniform static magnetic field in its inside space. For example, a permanent magnet, or a super conducting magnet is used as the static magnetic-field magnet 1.

The gradient magnetic-field coil 2 is formed in a hollow cylindrical shape, and is arranged inside the static magnetic-field magnet 1. The gradient magnetic-field coil 2 is formed of three coils in combination corresponding to x-axis, y-axis, and z-axis orthogonal to one another. The three coils generate gradient magnetic fields of which field strengths vary along three directions of the x-axis, y-axis, and z-axis, respectively, by individually receiving a current supply from the gradient magnetic-field power source 3, which will be described later. It is assumed that the z-axis direction is the same direction as that of the static magnetic field.

The gradient magnetic fields of the x-axis, y-axis, and z-axis generated by the gradient magnetic-field coil 2 correspond to, for example, a slice-selective gradient magnetic field Gs, a phase encoding gradient magnetic field Ge, and a readout gradient magnetic field Gr, respectively. The slice-selective gradient magnetic field Gs is used for arbitrarily setting a scan cross section. The phase encoding gradient magnetic field Ge is used for changing the phase of a magnetic resonance signal in accordance with a spatial position. The readout gradient magnetic field Gr is used for changing the frequency of an MR signal in accordance with a spatial position.

The gradient magnetic-field power source 3 supplies a current to the gradient magnetic-field coil 2 based on pulse-sequence execution data sent from the computer system.

The couch 4 includes a table 4a on which a subject P is to be placed, and under the control of the couch control unit 5, which will be described later, the couch 4 inserts the table 4a on which the subject P is placed, into a hole (a scanning space) of the gradient magnetic-field coil 2. Usually, the couch 4 is installed such that the longitudinal direction of the couch 4 is parallel to the central axis of the static magnetic-field magnet 1.

The couch control unit 5 moves the table 4a in the longitudinal direction and upward and downward by driving the couch 4.

The transmitting coil 6 is arranged inside the gradient magnetic-field coil 2, and generates a radio-frequency magnetic field by receiving supply of a radio-frequency pulse from the transmitting unit 7.

The transmitting unit 7 transmits a radio-frequency pulse corresponding to a Larmor frequency to the transmitting coil 6 based on pulse-sequence execution data sent from the computer system. The transmitting unit 7 includes an oscillating unit, a phase selecting unit, a frequency converting unit, an amplitude modulating unit, a radio-frequency power amplifying unit, and the like.

The oscillating unit generates a radio-frequency signal of a resonance frequency unique to a subject nucleus in the static magnetic field. The phase selecting unit selects a phase of the radio-frequency signal. The frequency converting unit converts the frequency of the radio-frequency signal output by the phase selecting unit. The amplitude modulating unit modulates the amplitude of the radio-frequency signal output by the frequency converting unit in accordance with, for example, a sinc function. The radio-frequency power amplifying unit amplifies the radio-frequency signal output by the amplitude modulating unit. As a result of operations performed by the above units, the transmitting unit 7 transmits a radio-frequency pulse corresponding to a Larmor frequency to the transmitting coil 6.

The receiving coil 8 is arranged inside the gradient magnetic-field coil 2, and receives an MR signal emitted from the subject P owing to an influence of the radio-frequency magnetic field described above. Specifically, the receiving coil 8 includes a plurality of elements each of which includes a coil for receiving an MR signal, and upon receiving an MR signal with the coil of each element, the receiving coil 8 outputs the received MR signal to the receiving unit 9.

The receiving unit 9 creates MR signal data based on the MR signal output by the receiving coil 8 based on pulse-sequence execution data sent from the computer system. After creating the MR signal data, the receiving unit 9 transmits the MR signal data to the computer system 10.

The computer system 10 performs total control of the MRI apparatus 100, data collection, image reconstruction, and the like. The computer system 10 includes an interface unit 11, a data collecting unit 12, a data processing unit 13, a storage unit 14, a display unit 15, an input unit 16, and a control unit 17.

The interface unit 11 is connected to the gradient magnetic-field power source 3, the couch control unit 5, the transmitting unit 7, and the receiving unit 9; and controls input and output of signals that are given and received between each of the connected units and the computer system 10.

The data collecting unit 12 collects MR signal data transmitted from the receiving unit 9 via the interface unit 11. When the MR signal data is collected, the data collecting unit 12 stores the collected MR signal data into the storage unit 14.

The data processing unit 13 performs post-processing, i.e., reconstruction processing, such as a Fourier transform, on MR signal data stored in the storage unit 14, and creates spectrum data or image data of a desired nuclear spin inside the subject P.

The storage unit 14 stores MR signal data collected by the data collecting unit 12, and image data created by the data processing unit 13, with respect to each subject P.

The display unit 15 displays various information, such as spectrum data or image data created by the data processing unit 13. A display device, such as a liquid crystal display, can be used as the display unit 15.

The input unit 16 receives various operations and information input from an operator. As the input unit 16, a pointing device, such as a mouse or a trackball, a selecting device, such as a mode switch, and an input device, such as a keyboard, can be used as required.

The control unit 17 includes a Central Processing Unit (CPU) and a memory, both of which are not shown, and controls the MRI apparatus 100 overall by controlling each unit described above.

Figure 2:
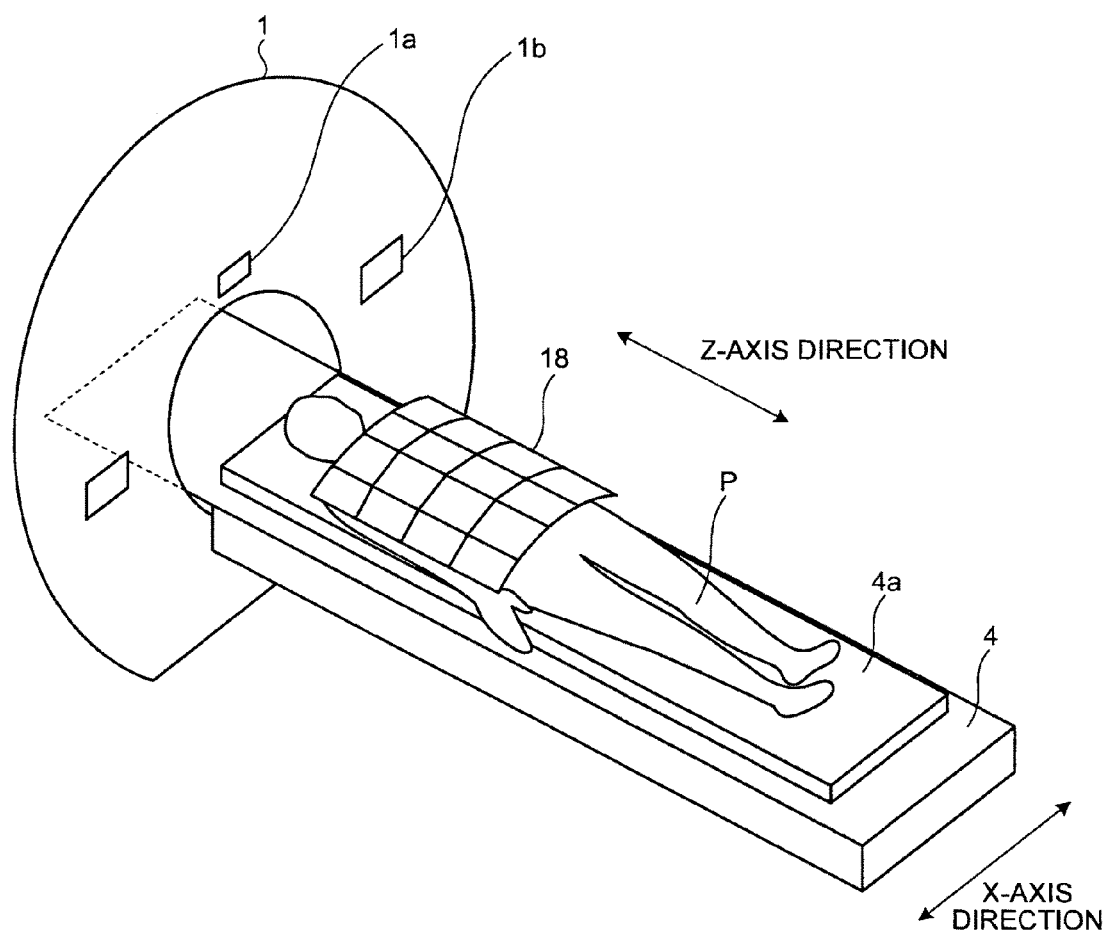
FIGS. 2 and 3 are schematic diagrams for explaining conventional positioning of a scan portion.
Figure 3:
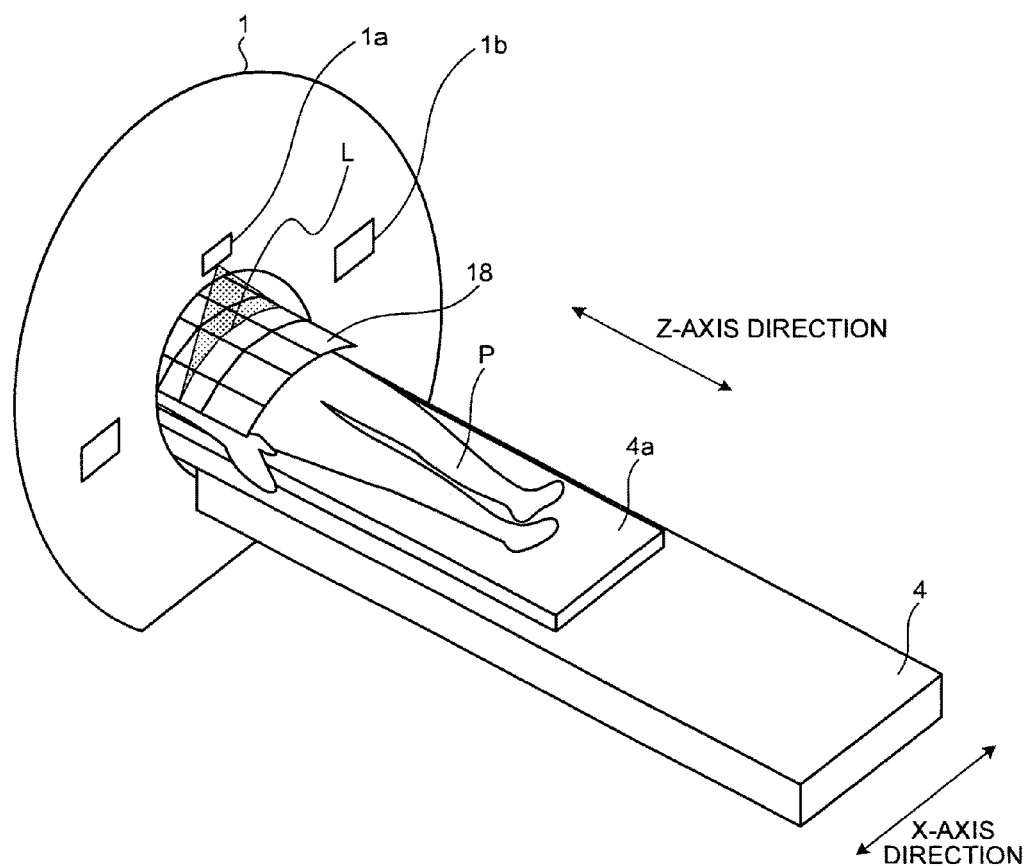

As described above, a general configuration of the MRI apparatus 100 according to the first embodiment has been explained. Prior to further explaining the MRI apparatus 100 below in detail, conventional positioning of a scan portion is explained below first with reference to FIGS. 2 and 3. FIGS. 2 and 3 are schematic diagrams for explaining conventional positioning of a scan portion.

The positioning of a scan portion explained below is setting a portion intended to be scanned in the subject P at the center of a magnetic field by moving the table 4a at the beginning of an examination after placing the subject P on the table 4a. The term "the center of a magnetic field" is not limited to one point with the highest uniformity of the magnetic field, but includes a region of a predetermined area in which the uniformity of the magnetic field is higher than a reference. Moreover, explained below is a case of using a receiving coil 18 that includes 16 elements in total arranged in four rows each in the x-axis direction and the z-axis direction, and it is assumed that a scan is performed by using the elements in the third row from the head of the subject P.

According to the conventional positioning, as shown in FIG. 2, the operator places the subject P on the table 4a that is installed on the couch 4 and movable in the horizontal direction, and then places the receiving coil 18 on a scan target portion, for example, a liver. When placing the receiving coil 18, the operator sets the receiving coil 18 onto the subject P such that the center of a region intended to be scanned in the subject P matches to the center in the table moving direction of a sensitive region of the elements in the third row.

Subsequently, the operator lights a projector 1a installed on the static magnetic-field magnet 1, and then moves the table 4a in the z-axis direction, as shown in FIG. 3. The operator then stops the table 4a once at a position at which a light L projected from the projector 1a matches with the center of the region intended to be scanned in the subject P. Accordingly, the MRI apparatus 100 recognizes a slide amount of the table 4a.

The operator then gives an instruction of an automatic slide of the table 4a to the MRI apparatus 100. When receiving the instruction, the MRI apparatus 100 moves the table 4a until the point set with the projector 1a matches to the center of the magnetic field. The above instructions of the lighting of the projector 1a, and the move, the stop, and the automatic slide of the table 4a are given by using buttons on an operation panel 1b.

In this way, the conventional positioning of a scan portion needs an operation of setting the center of the receiving coil onto the scan portion, an operation of positioning by using a projection light of the projector 1a, and an operation of moving the table 4a to the center of the magnetic field, and consequently requires time and efforts.

For this reason, the MRI apparatus 100 according to the first embodiment is configured to perform easily positioning of a scan portion and the center of the magnetic field even when using a plurality of coils as a coil that receives a magnetic resonance signal, by eliminating the need for the operation of positioning by using a projection light of the projector 1a.

Therefore, according to the MRI apparatus 100 according to the first embodiment, a plurality of buttons is provided on the receiving coil 8, and each of the buttons receives from the operator a selecting operation of selecting a coil from among the coils. The control unit 17 of the computer system 10 then moves the table 4a on which a subject is to be placed such that the coil selected by receiving the selecting operation via the button is positioned at the center of the magnetic field.

The MRI apparatus 100 is explained below in detail mainly about the receiving coil 8 and the computer system 10. First of all, the receiving coil 8 according to the first embodiment is explained below in detail with reference to FIGS. 4, 5, and 6. Although explained below is a case where the receiving coil 8 includes 16 elements in total that are arranged in four rows each in the x-axis direction and the z-axis direction, the number of elements included in the receiving coil 8 is not limited to this.

Figure 4:
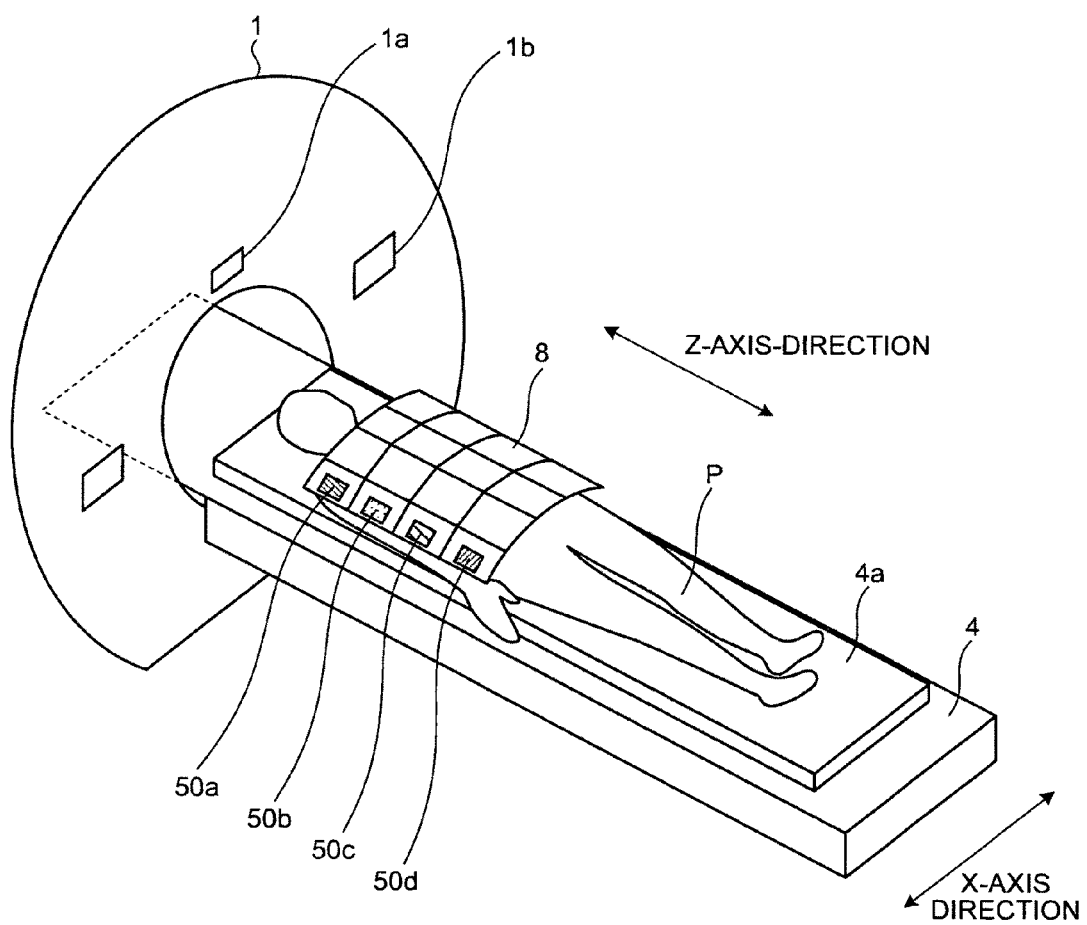
FIG. 4 is a schematic diagram of a state that a receiving coil is set on a subject on the MRI apparatus according to the first embodiment.

FIG. 4 is a schematic diagram of a state that the receiving coil 8 is set on the subject P on the MRI apparatus 100 according to the first embodiment. As shown in the figure, the receiving coil 8 is set, for example, on an abdomen of the subject P, and includes 16 elements arranged in four rows each in the x-axis direction and the z-axis direction, similarly to the receiving coil 18 shown in FIG. 2. Hereinafter, each group of elements arranged in parallel in the x-axis direction is called "section". In other words, the receiving coil 8 according to the first embodiment includes four rows of sections each of which includes four elements.

Figure 5:
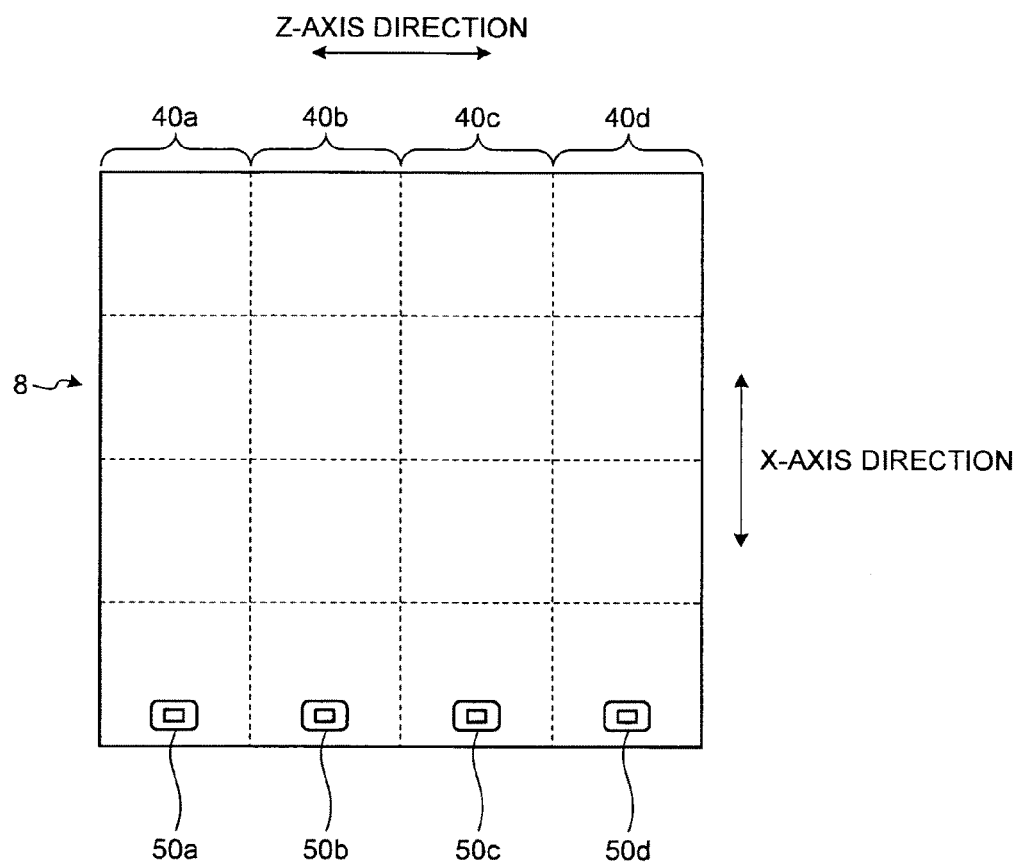
FIG. 5 is a schematic diagram of an appearance of the receiving coil according to the first embodiment.

According to the first embodiment, each section of the receiving coil 8 is provided with buttons 50a to 50d for the operator to select coils by section. FIG. 5 is a schematic diagram of an appearance of the receiving coil 8 according to the first embodiment. The figure depicts the upper surface of the receiving coil 8, and a direction extending between the right and the left of the figure corresponds to the z-axis direction. As shown in the figure, the receiving coil 8 includes four rows of sections 40a to 40d arranged in the z-axis direction, and each element at one end of each of the sections is provided with a button. Specifically, an element at one end of the section 40a is provided with the button 50a; an element at one end of the section 40b is provided with the button 50b; an element at one end of the section 40c is provided with the button 50c; and an element at one end of the section 40d is provided with the button 50d, respectively.

Each of the buttons 50a to 50d individually receives from the operator a selecting operation of selecting the section in which the button itself is provided. Specifically, each of the buttons 50a to 50d can take a state of ON or OFF individually; and when it is pressed by the operator (when it is turned to the ON state), it causes the receiving coil 8 to hold element selection information indicating that the section in which the button itself is provided is selected by the operator.

Figure 6:
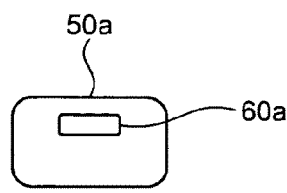
FIG. 6 is a schematic diagram of an indicator according to the first embodiment.

Moreover, each of the buttons 50a to 50d is provided with an indicator. FIG. 6 is a schematic diagram of an indicator according to the first embodiment. Each of the buttons 50a to 50d has the same configuration, so that a configuration of the button 50a is explained below as an example. As shown in the figure, the button 50a includes an indicator 60a.

The indicator 60a gives notice of a coil selected by receiving a selecting operation via the button 50a. For example, the indicator 60a is implemented by a Light Emitting Diode (LED), and lights up when the button 50a is pressed by the operator (when the button 50a is turned to the ON state).

In this way, when any of the buttons 50a to 50d is pressed, corresponding one of indicators 60a to 60d lights up, so that the operator can easily confirm a selected section (element). The indicators 60a to 60d are not necessarily provided on the buttons 50a to 50d, but can be provided independently in the vicinities of the buttons 50a to 50d, respectively.

Figure 7:
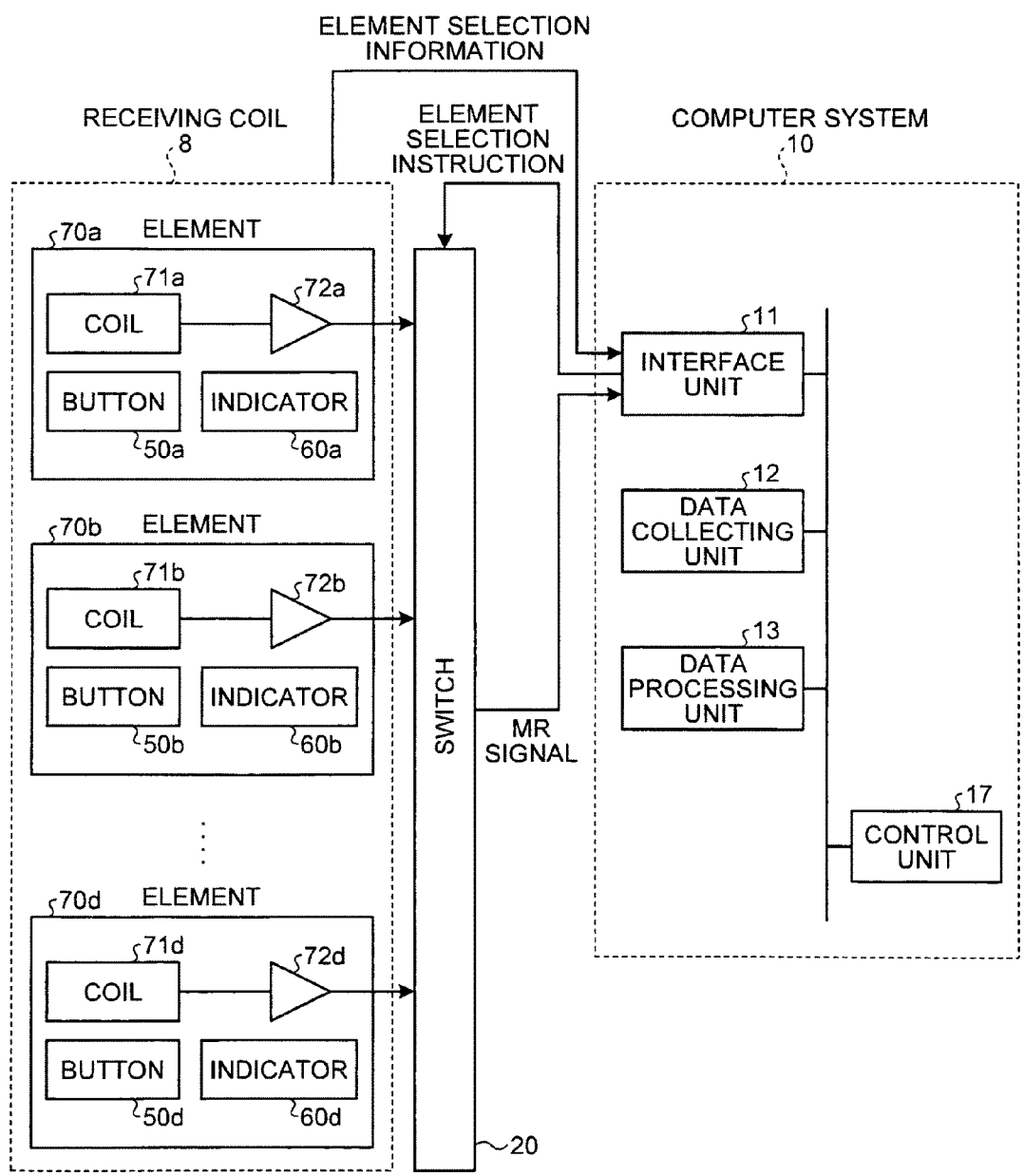
FIG. 7 is a functional block diagram of the receiving coil and a computer system according to the first embodiment.

Relation between the receiving coil 8 and the computer system 10 is explained below with reference to FIG. 7. FIG. 7 is a functional block diagram of the receiving coil 8 and the computer system 10 according to the first embodiment. As shown in the figure, the receiving coil 8 and the computer system 10 exchange various signals each other via a switch 20.

The switch 20 turns the coil of an element selected by the operator from among the elements 70a to 70d included in the receiving coil 8 to a state capable to receive a signal, under the control of the control unit 17 of the computer system 10. The switch 20 can be included in, for example, the receiving unit 9.

The receiving coil 8 includes a plurality of elements as described above. FIG. 7. depicts elements 70a to 70d provided with the buttons 50a to 50d, respectively, from among the elements. The element 70a includes a coil 71a, a signal amplifier 72a, the button 50a, and the indicator 60a. The element 70b includes a coil 71b, a signal amplifier 72b, the button 50b, and the indicator 60b; and the element 70d includes a coil 71d, a signal amplifier 72d, the button 50d, and the indicator 60d. Each of the elements 70a to 70d has the same configuration, so that a configuration of the element 70a is explained below as an example.

The button 50a is a button for selecting the section that includes the element 70a, and the indicator 60a lights up when the button 50a is pressed. Specifically, when the button 50a is pressed by the operator, the indicator 60a lights up, and the receiving coil 8 holds element selection information indicating that the section including the element 70a is selected.

The element selection information held by the receiving coil 8 is transmitted to the control unit 17 via the interface unit 11 in response to a request from the control unit 17 of the computer system 10. When the element selection information is transferred, the control unit 17 controls the switch 20 such that only coils of elements included in the section selected by the operator are turned capable to receive signals based on the element selection information. The control unit 17 transmits to the switch 20 via the interface unit 11 an element selection instruction of instructing the switch 20 to turn only the coils of the elements included in the selected section capable to receive signals.

The coil 71a receives an MR signal irradiated from the subject P. The signal amplifier 72a amplifies an MR signal received by the coil 71a, and transmits the amplified MR signal to the computer system 10 via the switch 20.

Figure 8:
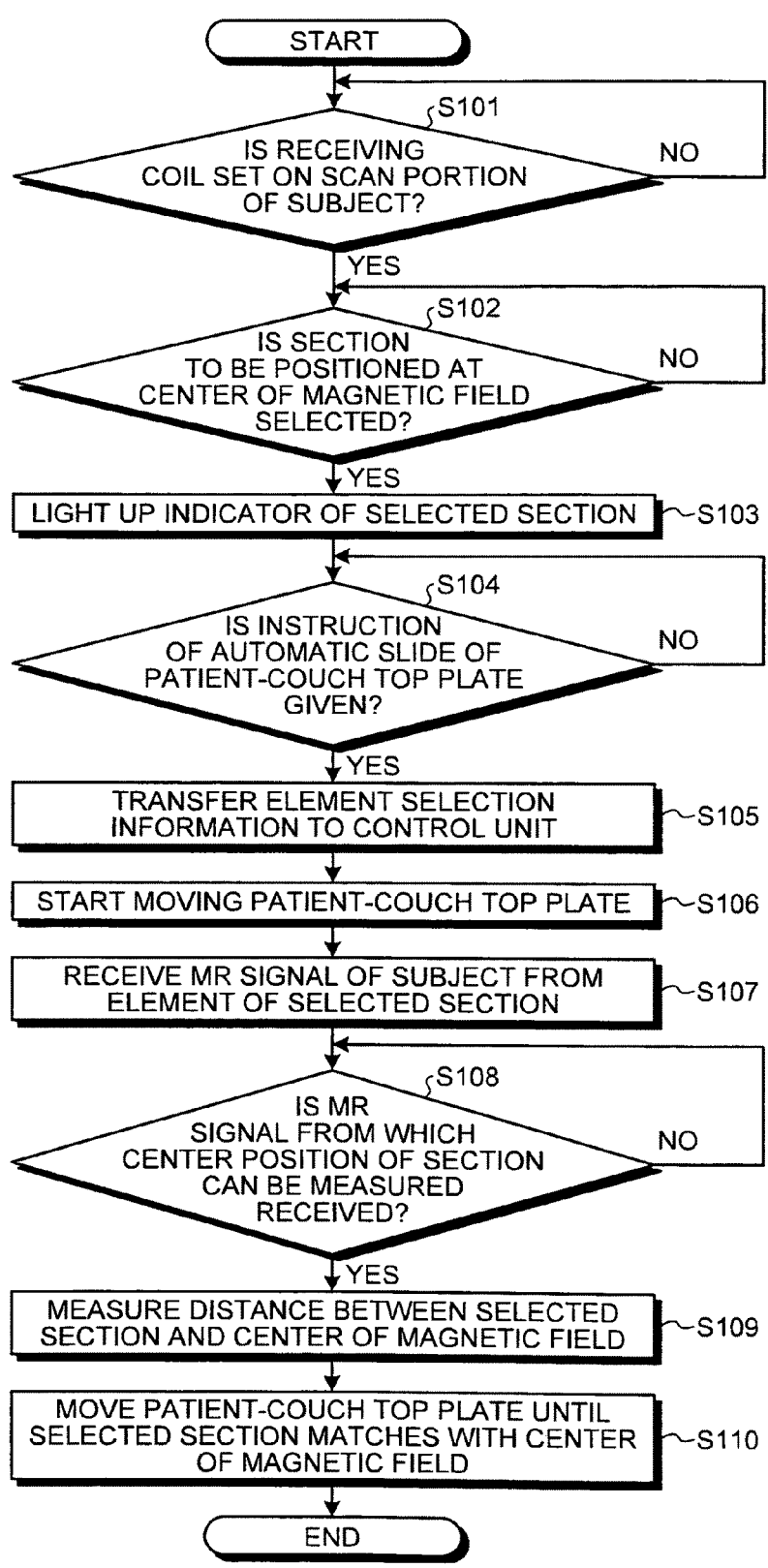
FIG. 8 is a flowchart of a flow of positioning of a scan portion performed by the MRI apparatus according to the first embodiment.

Positioning of a scan portion performed by the MRI apparatus 100 according to the first embodiment is explained below. FIG. 8 is a flowchart of a flow of positioning of a scan portion performed by the MRI apparatus 100 according to the first embodiment. Explained below is a case of performing a scan by using coils of elements included in the section 40c arranged in the third row from the head of the subject P.

As shown in the figure, according to the MRI apparatus 100 according to the first embodiment, to begin with the receiving coil 8 is set on a scan portion of the subject P by the operator (Yes at Step S101). A section to be positioned at the magnetic field center is then selected by the operator by pressing a button of a section positioned at the center of a region intended to be scanned in the subject P. In this case, the section 40c is selected by pressing the button 50c by the operator.

When the section 40c to be positioned at the magnetic field center is selected (Yes at Step S102), the indicator 60c of the selected section 40c lights up (Step S103).

Subsequently, when an instruction of an automatic slide of the table 4a is given by pressing a button on the operation panel 1b by the operator (Step S104), the control unit 17 of the computer system 10 requests the receiving coil 8 for element selection information. Accordingly, element selection information is transferred from the receiving coil 8 to the control unit 17 via the interface unit 11 (Step S105).

When the element selection information is transferred, the control unit 17 controls the switch 20 such that only the coils of the elements included in the section 40c are turned capable to receive signals, based on the element selection information. Accordingly, the coils of the elements included in the section 40c are turned to a state selected as an element to receive an MR signal.

Subsequently, the control unit 17 starts moving the table 4a in the z-axis direction (the longitudinal direction of the table 4a) by controlling the couch control unit 5 (Step S106), and receives an MR signal of the subject P with the coils of the elements included in the selected section 40c (Step S107).

At Step S107, the MR signal is received in a state as the coil is applied with a gradient magnetic field in the z-axis direction. Therefore, by performing a Fourier transformation of a signal received under the state that the section is in a sensitive region for the transmitting coil 6 by the coil of the element included in the selected section, a distance in the z-axis direction between the center of the selected section and the center of the magnetic field can be measured. The measurement method is basically similar to a method described in detail in JP-A H7-124135 (KOKAI).

According to the first embodiment, although not an MR signal from a marker attached on an element as described in JP-A H7-124135 (KOKAI), but an MR signal irradiated from the subject P is used, there is no fundamental difference in the principles of measurement. When using an MR signal from the subject P, a spectrum obtained through a Fourier transformation extends along the width of the sensitivity region of the receiving element in the z-axis direction. To improve measurement precision, for example, a signal exceeding a threshold higher than a noise component of the spectrum is extracted, and processed through processing of obtaining a half-width.

After that, when receiving an MR signal from which the center position of the section 40c can be measured (Yes at Step S108), the control unit 17 measures a distance in the z-axis direction between the center of the section 40c and the center of the magnetic field (Step S109). The control unit 17 then moves the table 4a in the z-axis direction until the center of the section 40c matches to the center of the magnetic field based on the measured distance, and stops the move of the table 4a when they match to each other (Step S110).

In this way, according to the positioning of a scan portion performed by the MRI apparatus 100 according to the first embodiment, after setting the receiving coil 8 onto the subject P, the operator presses a button of a section closest to a region that the operator intends to scan, i.e., a portion that the operator intends to set at the center of the magnetic field, and then only gives an instruction of an automatic slide of the table 4a by pressing a button on the operation panel 1b, accordingly, the scan portion is positioned at the center of the magnetic field. In other words, a bothersome positioning operation by using a projector that has been conventionally needed can be omitted.

As described above, according to the first embodiment, the sections 40a to 40d included in the receiving coil 8 are provided with the buttons 50a to 50d, respectively, and each of the buttons receives from the operator a selecting operation of selecting the section in which the button itself is provided. The control unit 17 of the computer system 10 then moves the table 4a such that the center of a section selected by receiving a selecting operation via the buttons 50a to 50d is positioned at the center of the magnetic field. Consequently, according to the first embodiment, operation of positioning by using a projection light of the projector 1a is not needed, and even when using a plurality of coils as a coil that receives an MR signal, positioning of a scan portion and the center of the magnetic field can be easily performed. Moreover, a total examination time can be reduced.

Although the first embodiment is explained above in a case of using one section for a scan, the present invention is not limited to this, and can be similarly applied to a case of using two or more sections. A case of using two or more sections is explained below as a second embodiment of the present invention.

A configuration of an MRI apparatus according to the second embodiment is basically similar to that of the MRI apparatus 100 according to the first embodiment, except that a configuration of buttons provided in the sections 40a to 40d of the receiving coil 8 and operation of the control unit 17 of the computer system 10 are different. Therefore, a configuration of buttons provided in the sections 40a to 40d of the receiving coil 8 according to the second embodiment, and positioning of a scan portion performed by the MRI apparatus 100 according to the second embodiment are explained below.

Figure 9:
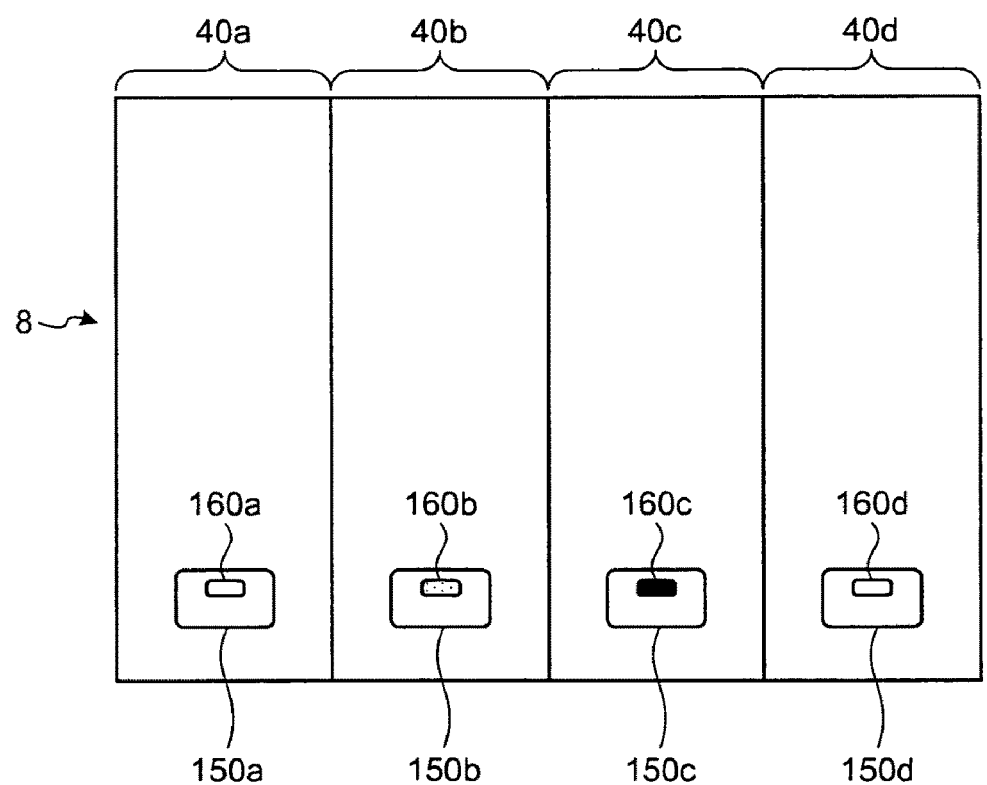
FIG. 9 is a schematic diagram of an appearance of a receiving coil according to a second embodiment of the present invention.

First of all, a configuration of buttons provided in the sections 40a to 40d according to the second embodiment is explained below with reference to FIG. 9. FIG. 9 is a schematic diagram of an appearance of the receiving coil 8 according to the second embodiment. As shown in the figure, the receiving coil 8 according to the second embodiment includes buttons 150a to 150d that are provided at respective one ends of the sections 40a to 40d, respectively, similarly to the first embodiment.

The buttons 150a to 150d receive from the operator a first selecting operation of selecting a section to be positioned at the center of the magnetic field, and a second selecting operation of selecting another section to be used for a scan in addition to the section selected by the first selecting operation, respectively.

Specifically, each of the buttons 150a to 150d can take each of three states, namely, a state 1, a state 2, and OFF, instead of each of the two states, ON and OFF only. A transition of the states takes place cyclically each time when each of the buttons 150a to 150d is pressed by the operator, and a change of the state is repeated from OFF, the state 1, the state 2, and then to OFF in order, in accordance with the number of times of pressing the button.

When the state of one of the buttons 150a to 150d turns to the state 1, the button causes the receiving coil 8 to hold element selection information indicating that the section in which the button itself is provided is a section to be positioned at the center of the magnetic field. On the other hand, when the state of one of the buttons 150a to 150d turns to the state 2, the button causes the receiving coil 8 to hold element selection information indicating that the section in which the button itself is provided is selected as a section to be additionally used for a scan.

Furthermore, similarly to the first embodiment, the buttons 150a to 150d are provided with indicators 160a to 160d, respectively. FIG. 9 is a schematic diagram that depicts indicators according to the second embodiment. As shown in the figure, according to the second embodiment, each of the indicators 160a to 160d gives notice of a section to be positioned at the center of the magnetic field, and another section to be additionally used for a scan, in a distinguishable manner.

Specifically, the indicators 160a to 160d can take each of three states, namely, a state 1 that it lights up in a first color (for example, red), a state 2 that it lights up in a second color (for example, blue), and a state of light-out, instead of each of only two states, light-up and light-out only. For example, when the button 150a turns to the state 1, the indicator 160a lights up in the first color (the state 1); when the button 150a turns to the state 2, the indicator 160a lights up in the second color (the state 2); and the button 150a turns to the OFF state, the indicator 160a lights out.

In this way, as the indicators 160a to 160d switch indications in accordance with respective states of the buttons 150a to 150d, the operator can easily confirm a section (or an element) to be positioned at the center of the magnetic field, and a section (or an element) to be used for a scan.

Figure 10:
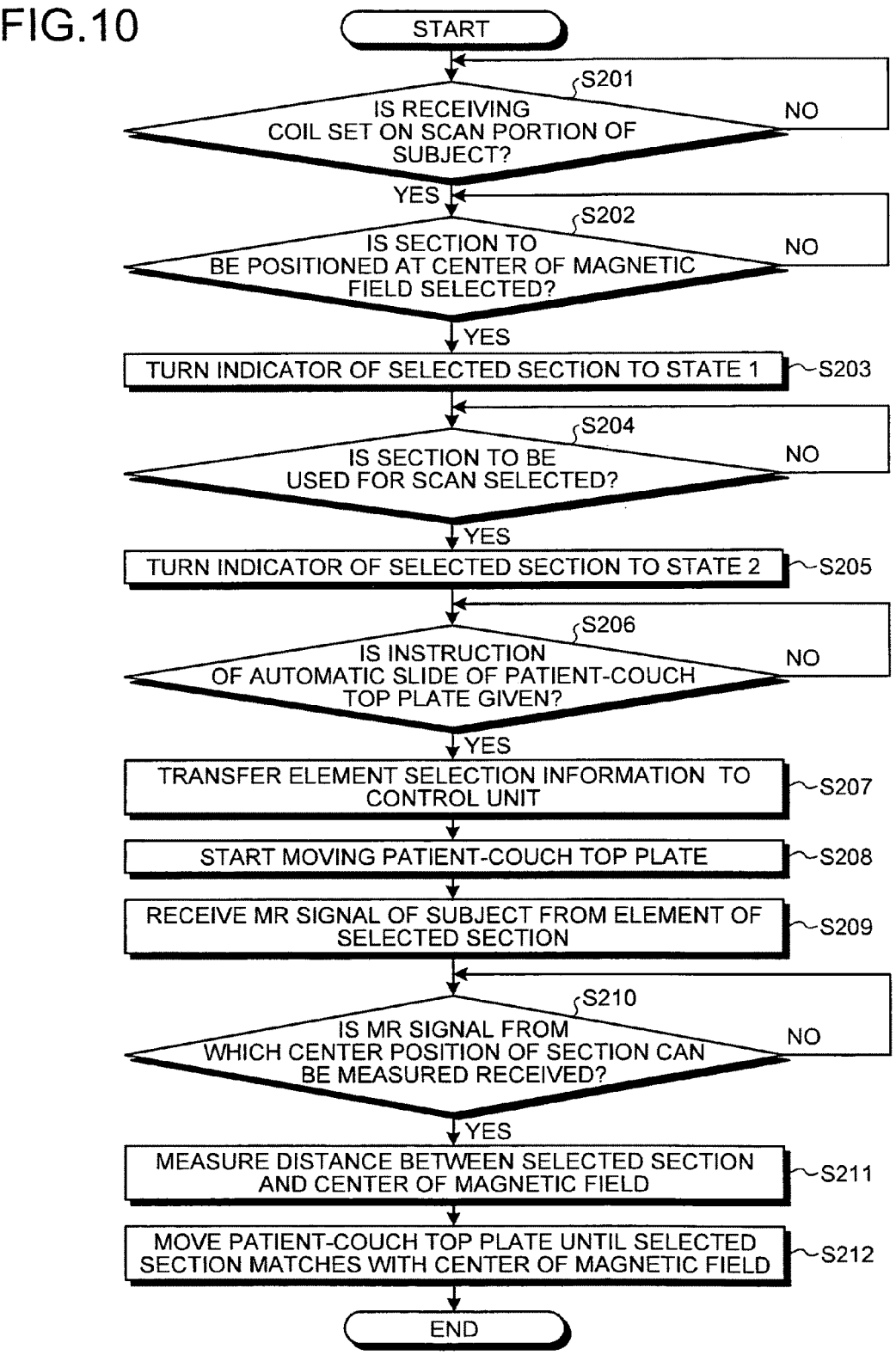
FIG. 10 is a flowchart of a flow of positioning of a scan portion performed by an MRI apparatus according to the second embodiment.

Positioning of a scan portion performed by the MRI apparatus 100 according to the second embodiment is explained below. FIG. 10 is a flowchart of a flow of positioning of a scan portion performed by the MRI apparatus 100 according to the second embodiment. Explained below is a case where the section 40c is to be positioned at the center of the magnetic field, and the section 40b is to be used for a scan in addition to the section 40c.

As shown in the figure, according to the MRI apparatus 100 according to the second embodiment, to begin with the receiving coil 8 is set on a scan portion of the subject P by the operator (Yes at Step S201). An element to be positioned at the magnetic field center is then selected by the operator by pressing a button of a section positioned at the center of a region intended to be scanned in the subject P. In this case, the section 40c is selected by pressing the button 150c once by the operator.

When the section 40c to be positioned at the magnetic field center is selected (Yes at Step S202), the indicator 160c of the selected section 40c turns to the state 1, and lights up in the first color (Step S203).

Subsequently, another element to be used for a scan is selected by the operator by pressing a button of another one of the elements twice. In this case, the section 40b is selected by pressing the button 150b twice by the operator.

When the section 40b is selected as a section to be used for the scan (Yes at Step S204), the indicator 160b of the selected section 40b turns to the state 2, and lights up in the second color (Step S205).

Subsequently, when an instruction of an automatic slide of the table 4a is given by pressing a button on the operation panel 1b by the operator (Step S206), the control unit 17 of the computer system 10 requests the receiving coil 8 for element selection information. Accordingly, element selection information is transferred from the receiving coil 8 to the control unit 17 via the interface unit 11 (Step S207).

When the element selection information is transferred, the control unit 17 controls the switch 20 such that only the coils of the elements included in the sections 40c and 40b are turned capable to receive signals, based on the element selection information. Accordingly, the coils of the elements included in the sections 40c and 40b are turned to a state selected as an element to receive an MR signal.

Subsequently, the control unit 17 starts moving the table 4a in the z-axis direction (the longitudinal direction of the table 4a) by controlling the couch control unit 5 (Step S208), and receives an MR signal of the subject P from the elements included in the selected sections 40c and 40b. (Step S209).

After that, when receiving an MR signal from which the center position of the section 40c can be measured (Yes at Step S210), the control unit 17 measures a distance in the z-axis direction between the center of the section 40c and the center of the magnetic field (Step S211). The control unit 17 then moves the table 4a in the z-axis direction until the center of the section 40c matches to the center of the magnetic field based on the measured distance, and stops the move of the table 4a when they match to each other (Step S212).

As described above, according to the second embodiment, each of the buttons 150a to 150d receives from the operator the first selecting operation of selecting a section to be used for a scan and to be positioned at the center of the magnetic field, and the second selecting operation of selecting another section to be used for the scan in addition to the section selected by the first selecting operation. The indicators 160a to 160d distinguishably indicate a section selected by receiving the first selecting operation and another section selected by receiving the second selecting operation, via the buttons 150a to 150d, respectively. Consequently, according to the second embodiment, elements included in two or more sections can be used for a scan, and selected sections can be easily confirmed.

Moreover, according to the second embodiment, coils of elements included in sections that are not selected by the operator (the sections 40a and 40d) are in a state of not receiving MR signal, so that interference of unwanted signal of other than the region of interest can be reduced, consequently, an image with less artifact can be obtained, compared with a case of receiving signals from the coils of the all elements.

A procedure of selecting a section is not limited to the one described above, and can be configured such that, for example, all sections to be used for a scan are selected by pressing a button once at first; then a section to be set at the center of the magnetic field is selected by further pressing a button once.

Otherwise, a button for specifying a section to be set at the center of the magnetic field and a button for specifying a section to be used for a scan can be separately provided in each section. The indicator is not limited to a multicolor Light Emitting Diode (LED), and can be configured to include two LEDs that indicate the state 1 and the state 2 respectively.

Figure 11:
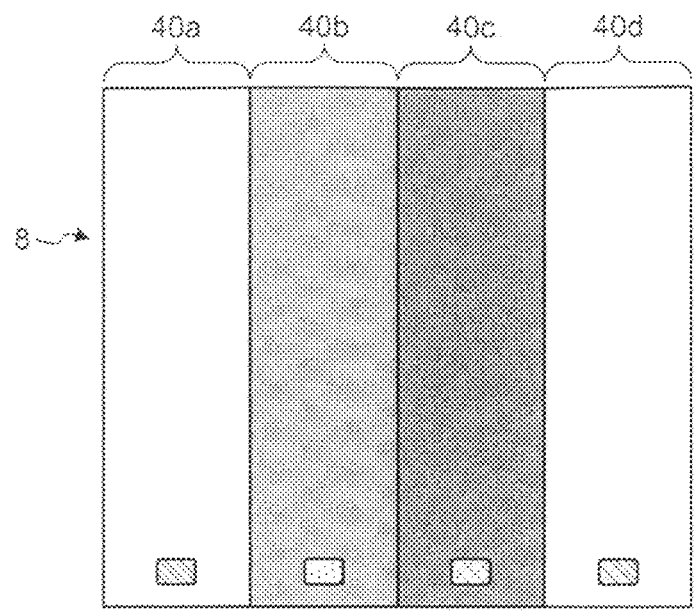
FIGS. 11 and 12 are schematic diagrams of a case where the surfaces of elements are caused to emit light.
Figure 12:
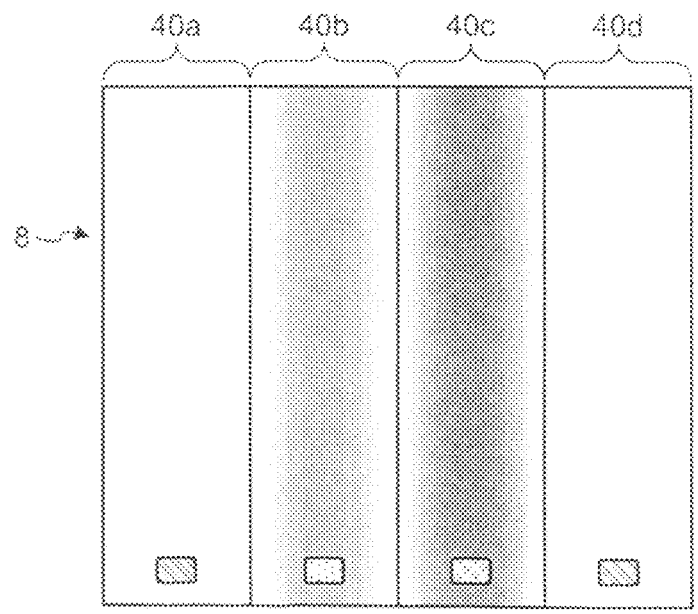

Although the above embodiments are explained in a case where an indicator is provided on an element at one end of each of the sections 40a to 40d, it can be configured such that the surface of an element is caused to emit light, for example. FIGS. 11 and 12 are schematic diagrams of a case where the surfaces of elements are caused to emit light.

In such case, for example, as shown in FIG. 11, the whole sensitive region of an element (coil) is caused to emit light by using a surface light-emitting element, such as an organic electroluminescent as an indicator. Accordingly, a reception sensitive region of elements (coils) to be used for a scan can be recognized by the operator more clearly. Alternatively, for example, as shown in FIG. 12, it can be configured such that under a state that the elements are selected, the color or strength of light emission is changed in accordance with a spatial distribution of reception sensitivities of the elements (coils). Accordingly, the coils can be set on the subject more precisely.

The embodiments are explained above in a case of selecting coils by section, i.e., a case where the buttons 50a to 50d are provided section by section on the receiving coil 8, and the control unit 17 moves the table 4a in z-axis direction (the longitudinal direction). However, the present invention is not limited to this. For example, if the MRI apparatus 100 includes a mechanism that can move the table 4a not only in the z-axis direction but also in the x-axis direction (the crosswise direction), a coil can be selected by element.

In such case, a button is provided on each element on the receiving coil 8, and the control unit 17 moves the table 4a in the z-axis direction and x-axis direction such that an element selected by the operator is to be positioned at the center of the magnetic field.

According to such configuration, the operator can select an element to be positioned at the center of the magnetic field from among a plurality of elements arranged in the x-axis direction. Accordingly, for example, when performing a scan of a heart, the operator can position the heart to be a scan portion at the center of the magnetic field easily and accurately, by selecting an element closest to the heart after setting the receiving coil on the subject.

Moreover, the embodiments are explained above in a case of using a receiving coil for abdomen; however, the present invention is not limited to this, and can be similarly applied to a case of using a receiving coil for other than abdomen. For example, a case where the present invention is applied to an MRI apparatus that includes a receiving coil arranged on the back side of a subject is explained below. Such receiving coil is used when scanning, for example, a spine.

Figure 13:
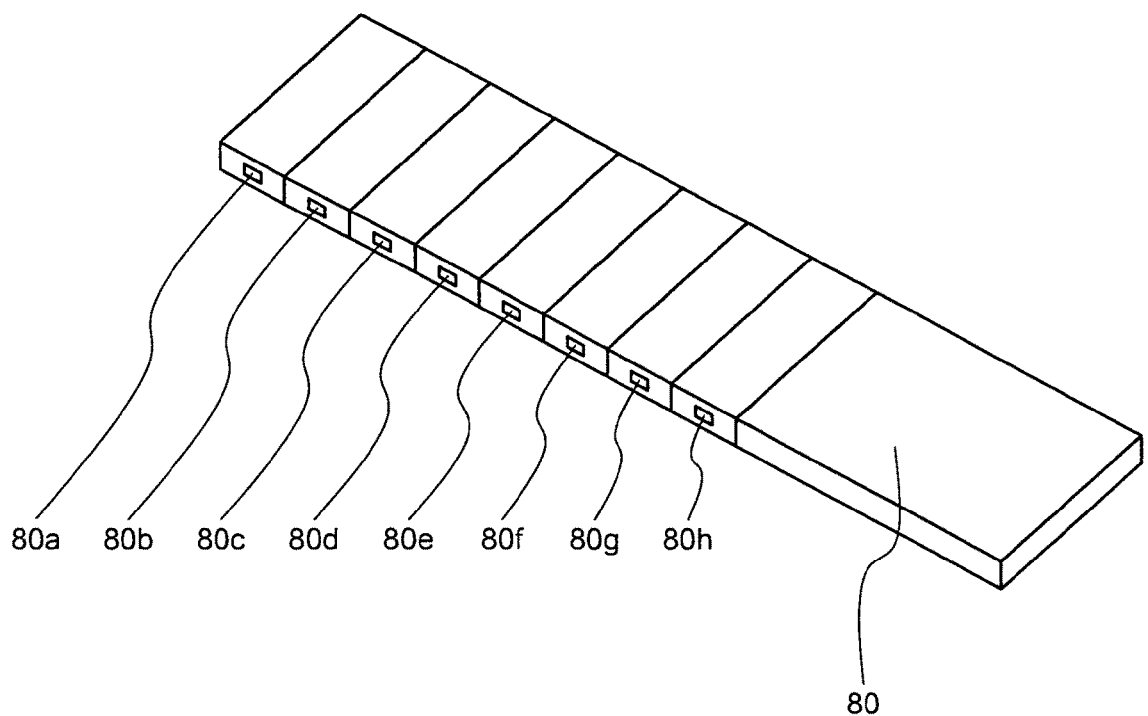
FIG. 13 is a schematic diagram of a receiving coil arranged on the back side of a subject.

FIG. 13 is a schematic diagram of a receiving coil arranged on the back side of a subject. A receiving coil 80 shown in the figure is implemented by embedding a plurality of coils in a table, and divided into a plurality of elements coil by coil. As shown in the figure, according to the receiving coil 80, similarly to the receiving coil 8 for abdomen as explained above, a plurality of buttons 80a to 80h is arranged in the z-axis direction.

A case where coils are embedded in a table as shown in the figure, or a case where a coil for spine that can be placed by moving in the z-axis direction is installed on a table is conceivable as a receiving coil arranged on the back side of a subject.

When the receiving coil is embedded in the table, or when the coil for spine cannot be installed at other than a specific position on the table, as the operator just selects an element to be positioned at the center of the magnetic field, so that a distance between the center of the magnetic field and the element to be positioned at the center of the magnetic field is settled. Therefore, in such case, there is no need to measure the distance by receiving an MR signal.

On the other hand, when the coil for spine can be installed at an arbitrary position in the z-axis direction, similarly to the case of the coil for abdomen explained in the first embodiment, positioning can be performed according to a method of measuring a distance between the center of the magnetic field and the element by receiving an MR signal.

Furthermore, the embodiments are explained above in a case where the receiving coil includes a plurality of elements; however, the present invention is not limited to this, and can be similarly applied to a case where a receiving coil includes only one element, or a case where only one array of elements is arranged in the z-axis direction.

Figure 14:
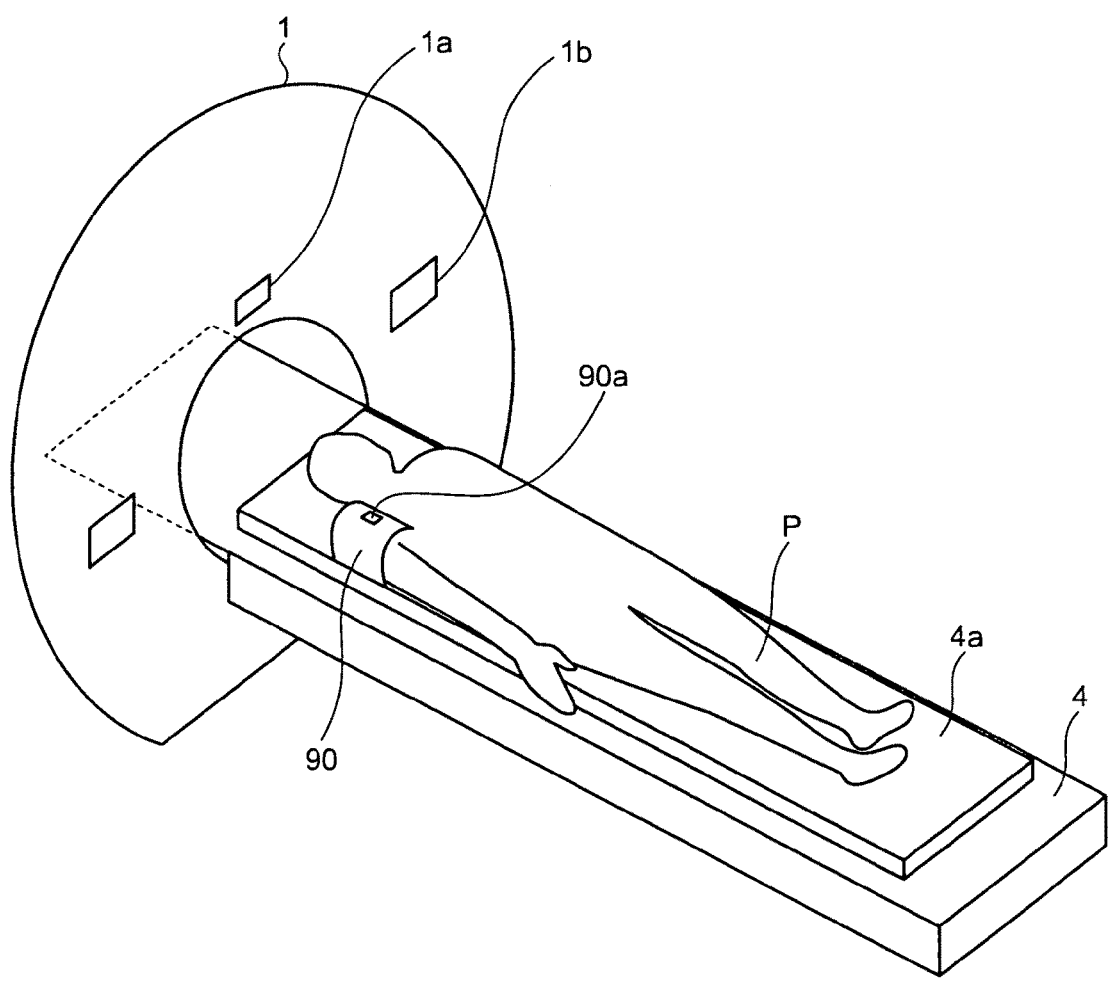
FIG. 14 is a schematic diagram of an example of a receiving coil that includes only one array of elements in the z-axis direction.
Figure 15:
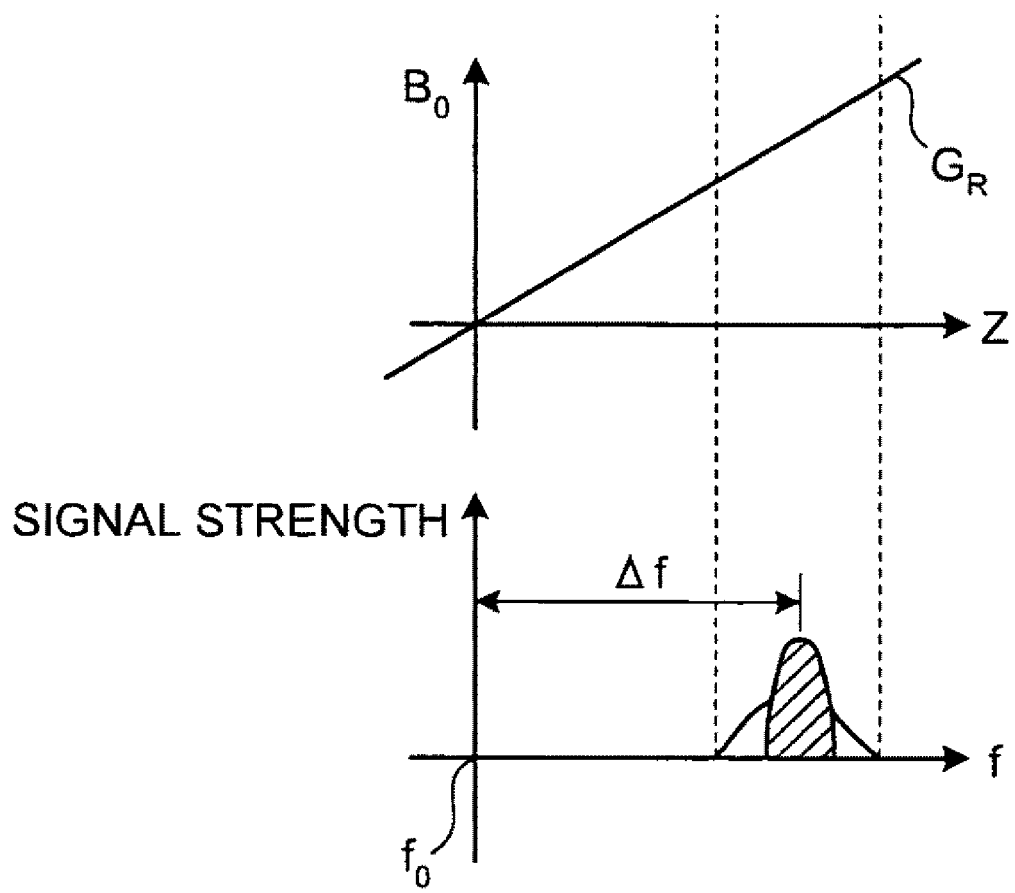
FIG. 15 is a schematic diagram for explaining a conventional method of positioning a receiving coil by using a marker.

FIG. 14 is a schematic diagram of an example of a receiving coil that includes only one array of elements in the z-axis direction. The figure depicts a case where a receiving coil for shoulder (hereinafter, "shoulder coil") 90 is set on the right shoulder of the subject P. In this case, it is assumed that the shoulder coil 90 is arranged only one in the z-axis direction. Even in such case, for example, as shown in FIG. 13, an element that can receive an MR signal is sometimes arranged on the table 4a on which the subject P is placed, in some cases.

In such case, to select the shoulder coil 90 to be actually used by distinguishing from another element arranged on the table 4a, a button 90a for selection is provided also on the shoulder coil 90. Regarding positioning of the subject P, even when positional relation between the shoulder coil 90 and the table 4a is not fixed, similarly to the first embodiment, the shoulder coil 90 can be moved to the center of the magnetic field by using an MR signal from the shoulder coil 90 without positioning operation by using a projector.

Moreover, the embodiments are explained above by assuming a case where the couch 4 is fixed on a gantry of the static magnetic-field magnet 1; however, the present invention is not limited to this, and can be similarly applied to a case where the couch 4 is detachable to the gantry of the static magnetic-field magnet 1. In such case, an element to be positioned at the center of the magnetic field and an element to be used for a scan can be set in advance outside an examination room, so that a total examination time can be reduced.

Furthermore, the embodiments are explained above in a case of using a button as a unit for receiving a selecting operation of selecting an element (or section) from an operator; however, the present invention is not limited to this. For example, when a connector for connecting the receiving coil to the main body of the MRI apparatus is provided on each element, the control unit 17 monitors connection conditions of the connectors, and performs positioning processing on an element of which connector is connected as a selected element.

Moreover, the embodiments are explained above in a case of selecting an element closest to a scan portion after setting the receiving coil on a subject; however, the present invention is not limited to this. For example, in a case of selecting an element of the receiving coil when setting scanning conditions, it can be configured such that the indicator of a selected element preliminarily lights up before the receiving coil is set on the subject.

In such case, for example, the computer system 10 transmits element selection information indicating the element selected by the operator while setting the scanning conditions to the receiving coil via a connector. The receiving coil then causes the indicator of the selected element to lights up based on the transmitted element selection information. For example, when a wireless transmitting unit is provided in each of the computer system 10 and the receiving coil, it can be configured such that the computer system 10 transmits element selection information to the receiving coil via wireless transmission.

Usually, the static magnetic-field magnet 1 and the couch 4 are often installed in a different room from the computer system 10 in many cases. For this reason, the operator sometimes forgets which element is selected in some cases, while the operator is moving to the room in which the static magnetic-field magnet 1 and the couch 4 are installed after setting scanning conditions by using the computer system 10. In such case, if the indicator of a selected element preliminarily lights up, the operator can set the receiving coil at an appropriate position on the subject without mistaking the selected element.

The embodiments are explained above in a case of selecting an element (or section) of the receiving coil by turning a button to the ON state by the operator. However, for example, there is a possibility that the operator forgets to turn the button of a coil used for a scan to the OFF state, when the scan is finished. In such case, it is conceivable that an unexpected element is positioned at the center of the magnetic field in the next scan, or that an unexpected element is used for the next scan.

Therefore, for example, it can be configured to cancel automatically at a certain moment a state that an element is selected. In such case, for example, at a moment after the control unit 17 of the computer system 10 has moved the table 4a until an element selected by the operator is positioned at the center of the magnetic field, the control unit 17 turns off the button of the selected element, and deletes the element selection information held by the receiving coil.

Alternatively, for example, at a moment when the control unit 17 of the computer system 10 starts moving the table 4a after acquiring element selection information from the receiving coil, the control unit 17 can turn off the button of the selected element, and can delete the element selection information held by the receiving coil.

Accordingly, even if the operator forgets to turn the button of a coil used for a scan to the OFF state when the scan is finished, a mistake of positioning an unexpected element at the center of the magnetic field in the next scan, or a mistake of using an unexpected element for the next scan can be avoided.

Furthermore, the second embodiment is explained above in a case where the first selecting operation of selecting a section to be used for a scan and to be positioned at the center of the magnetic field, and the second selecting operation of selecting another section to be used for the scan in addition to the section selected by the first selecting operation are received respectively, and then the table is moved such that the section selected by receiving the first selecting operation is to be positioned at the center of the magnetic field.

However, for example, when using a plurality of sections (or elements) for a scan, the table can be moved such that the center of the whole of the sections selected by the operator is to be positioned at the center of the magnetic field.

In such case, for example, the storage unit 14 of the computer system 10 preliminarily stores information about positional relation of sections (or elements) included in a receiving coil as coil information with respect to each type of receiving coils. Moreover, the control unit 17 detects the type of a receiving coil when the receiving coil is connected to a connector. When an MR signal is received by selected sections as assumed to be used for a scan, the control unit 17 calculates a distance in the z-axis direction between the center of the whole of the selected sections and the center of the magnetic field, by referring to the coil information stored in the storage unit 14. The control unit 17 then moves the table 4a in the z-axis direction until the center of the whole of the selected sections matches to the center of the magnetic field based on the measured distance.

Accordingly, when an odd number of sections are selected by the operator, the center of a section positioned at the center of the selected sections is positioned at the center of the magnetic field. By contrast, when an even number of sections are selected, the middle of two sections positioned at the center of the selected sections is positioned at the center of the magnetic field.

Moreover, in this case, any button that can take two states of ON and OFF can be used as a button for selecting a section instead of using a button that can take three states, the state 1, the state 2, and OFF, as described in the second embodiment, and the center of the whole of the sections is automatically positioned at the center of the magnetic field by only selecting sections to be used for a scan by the operator. Accordingly, when using a plurality of sections for a scan, positioning of a scan portion and the center of the magnetic field can be more easily performed.

As described above, the magnetic resonance imaging apparatus and the control method of the magnetic resonance imaging apparatus according to the embodiments of the present invention are useful when a plurality of receiving coils or a receiving coil including a plurality of elements is used for scan, and particularly suitable when a total examination time is required to be reduced by reducing operations required for positioning a scan portion.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A magnetic resonance imaging (MRI) apparatus comprising:
    a receiving radio frequency (RF) coil assembly that includes a plurality of RF coils configured to receive magnetic resonance signals irradiated from a subject;
    a manually-operated coil selection unit disposed in the receiving coil assembly, and configured to receive an operator's selection actuation operation selecting at least one RF coil from among the plurality of RF coils; and
    a control unit that thereafter automatically moves a table on which the subject and the RF coil assembly are placed to cause the RF coil(s) selected by the operator's selecting operation to be positioned at a center of a magnetic field within an MRI apparatus.

2. The apparatus according to claim 1, further comprising a selected-coil notifying unit that gives an operator notice of the currently selected coil(s).

3. The apparatus according to claim 1, wherein:
    the manually-operated coil selecting unit is configured to effect a first operator selecting operation selecting at least a first one of said RF coils to be used for a scan and to be positioned at the center of the magnetic field, and a second operator selecting operation selecting at least a second different one of said RF coils to be used for a scan in addition to the coil(s) selected by the first selecting operation, and
    the control unit first moves the table to cause the RF coil(s) selected by the first selecting operation to be positioned at the center of the magnetic field.

4. The apparatus according to claim 3, further comprising:
    a selected-coil notifying unit that gives an operator notice of (a) the RF coil(s) selected by the first selecting operation, and (b) the RF coil(s) selected by the second selecting operation in a mutually distinguishable manner.

5. The apparatus according to claim 2, wherein:
    the selected-coil notifying unit changes a mode of operator notice in accordance with one of (a) a sensitive region and (b) a spatial distribution of sensitivity of the selected coil(s).

6. The apparatus according to claim 4, wherein:
    the selected-coil notifying unit changes a mode of operator notice in accordance with one of (a) a sensitive region and (b) a spatial distribution of sensitivity of the selected coil(s).

7. The apparatus according to claim 1, wherein:
    the control unit is configured to measure a positional relationship between the center of the magnetic field and the selected coil(s) based on a magnetic resonance signal received by the coil(s), and to move the table based on the measured positional relationship.

8. The apparatus according to claim 2, wherein:
    the control unit is configured to measure a positional relationship between the center of the magnetic field and the selected coil(s) based on a magnetic resonance signal received by the coil(s), and to move the table based on the measured positional relationship.

9. The apparatus according to claim 3, wherein:
    the control unit is configured to measure a positional relationship between the center of the magnetic field and the selected coil(s) based on a magnetic resonance signal received by the coil(s), and to move the table based on the measured positional relationship.

10. The apparatus according to claim 4, wherein:
    the control unit is configured to measure a positional relationship between the center of the magnetic field and the selected coil(s) based on a magnetic resonance signal received by the coil(s), and to move the table based on the measured positional relationship.

11. The apparatus according to claim 5, wherein:
    the control unit is configured to measure a positional relationship between the center of the magnetic field and the selected coil(s) based on a magnetic resonance signal received by the coil(s), and to move the table based on the measured positional relationship.

12. The apparatus according to claim 1, wherein:
the plurality of RF coils are arranged in parallel along a longitudinal direction of the table, and
the control unit is configured to move the table along the longitudinal direction.

13. The apparatus according to claim 2, wherein:
the plurality of RF coils are arranged in parallel along a longitudinal direction of the table, and
the control unit is configured to move the table along the longitudinal direction.

14. The apparatus according to claim 3, wherein:
the plurality of RF coils are arranged in parallel along a longitudinal direction of the table, and
the control unit is configured to move the table along the longitudinal direction.

15. The apparatus according to claim 4, wherein:
the plurality of RF coils that are arranged in parallel along a longitudinal direction of the table, and
the control unit is configured to move the table along the longitudinal direction.

16. The apparatus according to claim 1, wherein:
the plurality of RF coils that are arranged in parallel along a crosswise direction of the table, and
the control unit is configured to move the table along the crosswise direction.

17. The apparatus according to claim 2, wherein:
the plurality of RF coils that are arranged in parallel along a crosswise direction of the table, and
the control unit is configured to move the table along the crosswise direction.

18. The apparatus according to claim 3, wherein:
the plurality of RF coils that are arranged in parallel along a crosswise direction of the table, and
the control unit is configured to move the table along the crosswise direction.

19. The apparatus according to claim 4, wherein:
the plurality of RF coils that are arranged in parallel along a crosswise direction of the table, and
the control unit is configured to move the table along the crosswise direction.

20. A method of controlling a magnetic resonance imaging (MRI) apparatus, the method comprising:
receiving an operator selecting operation selecting at least one radio frequency (RF) coil from among a plurality of RF coils included in a receiving RF coil assembly that receives magnetic resonance signals irradiated from a subject, and
automatically moving a table on which the subject and said RF coil assembly are placed to cause the selected coil(s) to be positioned at a center of a magnetic field.

21. The apparatus according to claim 1, wherein:
the control unit, upon a predetermined condition, automatically cancels a coil selection state.

22. The apparatus according to claim 21, wherein:
the control unit cancels a coil selection state when the selected coil(s) is positioned at the center of the magnetic field.

23. The apparatus according to claim 21, wherein:
the control unit cancels a coil selection state when the control unit starts moving the table after acquiring coil selection information from the selected receiving coil (s).

24. The apparatus according to claim 21, wherein:
the coil selecting unit includes a manually operable button located on the receiving coil assembly which selects at least two states of ON and OFF for selecting a coil on which the button itself is provided, and
the control unit moves the table to cause a coil on which the button is in the ON state to be positioned at the center of the magnetic field when automatic positioning is requested until the button is turned to the OFF state.

25. The apparatus according to claim 1, wherein:
when a plurality of RF coils are selected by the operator, the control unit moves the table such that a center of the whole of the selected coils is positioned at the center of the magnetic field.

26. The apparatus according to claim 1, wherein:
the coil selecting unit includes a plurality of buttons, each button being provided on each said RF coil and being configured to take at least two states of ON and OFF for selecting a coil on which the button itself is provided and
the control unit moves the table to cause the coil on which the button is in the ON state to be positioned at the center of the magnetic field.

* * * * *